(12) United States Patent
Jiang et al.

(10) Patent No.: US 8,447,402 B1
(45) Date of Patent: *May 21, 2013

(54) ZIRCONIA TO PLATINUM ASSEMBLY USING A TITANIUM CONNECTOR

(75) Inventors: Guangqiang Jiang, Santa Clarita, CA (US); Attila Antalfy, Valencia, CA (US)

(73) Assignee: Alfred E. Mann Foundation For Scientific Research, Santa Clarita, CA (US)

( * ) Notice: Subject to any disclaimer, the term of this patent is extended or adjusted under 35 U.S.C. 154(b) by 1709 days.

This patent is subject to a terminal disclaimer.

(21) Appl. No.: 11/691,293

(22) Filed: Mar. 26, 2007

Related U.S. Application Data

(60) Provisional application No. 60/787,875, filed on Mar. 31, 2006.

(51) Int. Cl.
*A61N 1/375* (2006.01)
*A61N 1/00* (2006.01)
*B32B 15/04* (2006.01)
*B23K 1/00* (2006.01)

(52) U.S. Cl.
USPC .............. 607/36; 607/115; 600/373; 428/621

(58) Field of Classification Search .............. 607/2, 121; 600/301; 604/20; 128/899
See application file for complete search history.

(56) References Cited

U.S. PATENT DOCUMENTS

| | | | | | |
|---|---|---|---|---|---|
| 3,395,993 | A | * | 8/1968 | Bristow | ........................ 428/633 |
| 4,197,957 | A | * | 4/1980 | Buhrer | ....................... 220/2.1 R |
| 4,516,820 | A | * | 5/1985 | Kuzma | ......................... 439/289 |
| 4,785,827 | A | * | 11/1988 | Fischer | ........................... 607/57 |
| 4,991,582 | A | * | 2/1991 | Byers et al. | ....................... 607/2 |
| 5,193,540 | A | * | 3/1993 | Schulman et al. | .............. 607/61 |
| 5,782,891 | A | * | 7/1998 | Hassler et al. | .................. 607/36 |
| 6,989,200 | B2 | * | 1/2006 | Byers et al. | ..................... 428/621 |
| 7,103,408 | B2 | * | 9/2006 | Haller et al. | ....................... 607/2 |
| 7,114,502 | B2 | * | 10/2006 | Schulman et al. | ............ 128/899 |
| 7,132,173 | B2 | * | 11/2006 | Daulton | ........................ 428/621 |
| 7,166,388 | B2 | * | 1/2007 | Tsukamoto et al. | .......... 429/175 |
| 7,177,698 | B2 | * | 2/2007 | Klosterman et al. | ............ 607/60 |
| 2005/0240229 | A1 | * | 10/2005 | Whitehurst et al. | .............. 607/2 |

OTHER PUBLICATIONS

J. H. Schulman, J. P. Mobley, J. Wolfe, E. Regev, C. Y. Perron, R. Ananth, E. Matei, A. Glukhovsky, R. Davis, "Battery Powered BION FES Network", Sep. 1-5, 2004, Proceedings of the 26th Annual International Conference of the IEEE EMBS, 0-7803-8439-3/04, pp. 4283-4286.*

* cited by examiner

*Primary Examiner* — Carl H Layno
*Assistant Examiner* — Erin Piateski
(74) *Attorney, Agent, or Firm* — Gary D. Schnittgrund

(57) ABSTRACT

The invention is a component assembly and method of hermetically bonding a ceramic part to a metal part by welding and brazing a component assembly comprised of metal parts, a ceramic part, and an intermediate metal ferrule. The ceramic part is preferably a hollow tube of partially-stabilized zirconia that is brazed to an alignment ferrule that is preferably titanium or a titanium alloy, such as Ti-6Al-4V. On one end the component assembly is brazed to an end cap for closure. On the other end the alignment ferrule is preferably brazed to a ring that is preferably comprised of a noble metal, such as platinum, iridium, or alloys of platinum and iridium. The ring is then laser welded to an eyelet that is preferably comprised of a noble metal.

12 Claims, 2 Drawing Sheets

ZIRCONIA TO PLATINUM ASSEMBLY USING A TITANIUM CONNECTOR

CROSS-REFERENCE TO RELATED APPLICATION

This application claims the benefit of U.S. Provisional Application Ser. No. 60/787,875, filed on Mar. 31, 2006.

BACKGROUND OF THE INVENTION

1. Field of the Invention

This invention relates to a bonded assembly of zirconia ceramic to platinum or other noble metal that employs an alignment ferrule comprised of titanium or an alloy of titanium. The assembly is suitable for implantation in living tissue.

2. Description of Related Art Including Information Disclosed Under 37 CFR 1.97 and 1.98

This invention is concerned with achieving a hermetic bond for an implantable medical device, where the bond is between a ceramic, preferably partially stabilized zirconia, and a noble metal, preferably platinum. A titanium or titanium alloy alignment ferrule provides a transition to allow a noble metal ring to be brazed to the alignment ferrule which is in turn welded to a noble metal eyelet or end cap. It is known that noble metal can be bonded by brazing to ceramic, U.S. Pat. No. 6,989,200. However, this has only been successful with butt joints and has not been previously demonstrated with step and lap joints, as required for certain applications such as where parts require self-centering.

It is desired that the end cap and eyelet, which are electrodes for contact with living tissue when implanted, can sustain high current density and have low impedance, as available only with noble metals, such as platinum, iridium, or their alloys.

DETAILED DESCRIPTION OF THE INVENTION

Figure 1:
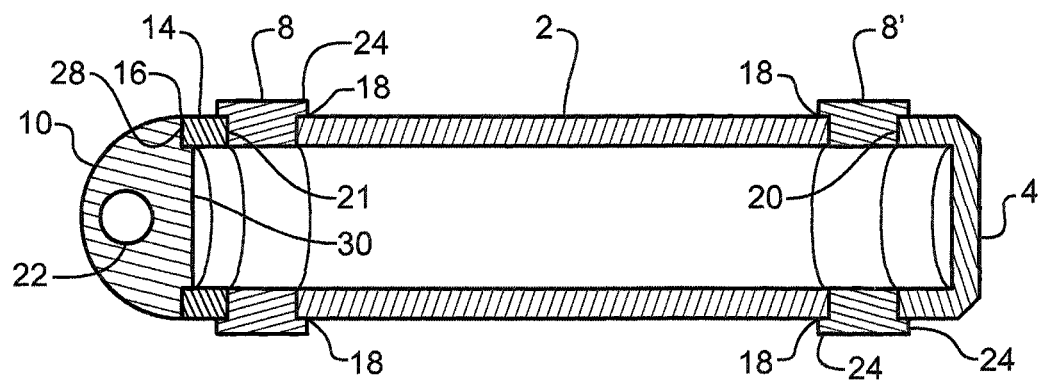
FIG. 1 illustrates a cross-sectional view of a hollow microstimulator case assembly illustrating the improved attachment.

FIG. 1 provides a cross-sectional view of a preferred embodiment of the component assembly 12. It consists of a ceramic article, preferably a hollow ceramic tube 2 that is bonded to an alignment ferrule 8, 8' which may be placed on each end, a first and a second end, respectively, of the hollow ceramic tube 2 by brazing to form braze joint 18. The ceramic is preferably comprised of a partially stabilized tetragonal zirconia polycrystal, which contains about 3 volume percent yttria. U.S. Pat. Nos. 3,594,895; 3,994,430; 6,221,513; 6,521,350; 6,986,453; and 6,989,200 disclose applicable brazing methods and are incorporated herein by reference in their entirety. The alignment ferrule(s) 8, 8' are preferably comprised of titanium or a titanium alloy, such as Ti-6Al-4V. The ceramic tube is preferably a hollow cylinder but may be solid in an alternative embodiment.

The alignment ferrule 8 is joined to a ring 14, which is optionally preferably hollow, and may be solid. Ring 14 is preferably comprised of a noble metal which is biocompatible, such as platinum, iridium, and alloys of platinum and iridium, such as platinum-10 percent by weight iridium.

An eyelet 10 is metallurgically joined to the ring 14, preferably by welding and more preferably by laser welding. As presented, the eyelet 10 optionally has an eyelet hole 22 which facilitates attachment of a removal device, such as a string. In an embodiment wherein the alignment ferrule 8 and the ring 14 are hollow, then the eyelet 10 serves to close-out and hermetically seal the hollow ceramic tube 2, thereby protecting any electronics package that is in tube 2.

As presented in FIG. 1, the eyelet 10 would be associated with and would therefore act as the stimulation anode in an implantable biomedical microstimulator, which results when electronic circuitry is placed inside the ceramic tube 2. Known miniature monitoring and/or stimulating devices for implantation in a living body are disclosed in U.S. Pat. Nos. 6,164,284; 6,185,452; 6,208,894; 6,315,721; 6,564,807; and their progeny, each of which is incorporated herein by reference in its entirety. Typical dimensions for this device are about 5 to 60 mm in length and about 1 to 6 mm in diameter. A coating of iridium may alternately be applied to the titanium alignment ferrule 8 to facilitate tissue contact at the anode end of the component assembly 12.

The second end of the ceramic tube 2 is bonded, preferably by brazing, to an alignment ferrule 8'. The alignment ferrule 8' is bonded, preferably by brazing to an end cap 4, which in a preferred embodiment is comprised of a noble metal, such as platinum, iridium, and alloys of platinum and iridium, such as platinum-10 percent by weight iridium. The end cap 4 is preferably the cathode end of the stimulator, as discussed above.

The joining of the alignment ferrule(s) 8, 8' by brazing to the zirconia tube 2 is accomplished to yield a braze joint 18. In a preferred embodiment nickel foil is the interlayer braze material. In an alternate embodiment, the interlayer braze foil is comprised of a laminate of nickel and titanium. One preferred laminate is obtained from Morgan Advanced Ceramics and is called TiNi-50.

At the second end, the alignment ferrule 8' is preferably bonded by brazing with nickel foil as the interlayer thereby creating braze joint 20 between alignment ferrule 8' and end cap 4.

At the first end the ring 14 is braze bonded using a nickel foil to form braze joint 21 between alignment ferrule 8 and platinum ring 14. The platinum ring 14 is welded by laser to form laser weldment 16 to the platinum eyelet 10.

Figure 2:
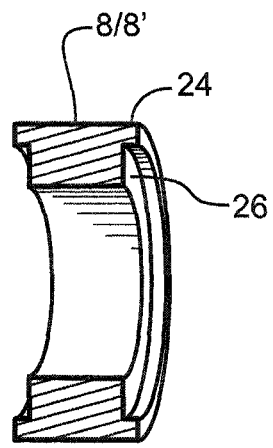
FIG. 2 illustrates a perspective view of an alignment ferrule.

The alignment ferrule(s) 8, 8' are presented in FIG. 2. As discussed, the ferrule is preferably comprised of titanium or in an alternative embodiment Ti-6AL-4V. Either material can be brazed to zirconia ceramic and brazed to platinum or another of the noble metals. A further novel feature of the alignment ferrule 8, 8' is that it is self-aligning in that the lip 24 which in combination with the ferrule face 26 provides a positive alignment of the ferrule 8, 8' on both the ceramic tube and the mating metal part. For example alignment ferrule 8' mates in excellent alignment, without use of a fixture, to the tube 2 and to the end cap 4. Similarly, the alignment ferrule 8 mates to the tube 2 as well as to the ring 14 without use of a fixture.

Figure 3:
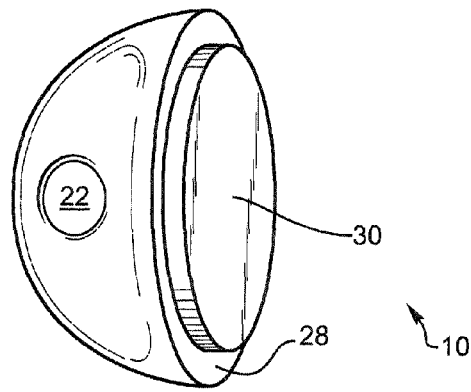
FIG. 3 illustrates a perspective view of an eyelet.

The eyelet 10 also is self-aligning with the ring 14, FIG. 3. The eyelet 10 has a raised alignment tab 30 which is sized to fit inside the ring 14, thereby assuring excellent alignment without the use of a fixture for the welding process. The alignment face 28 of the eyelet 10 mates with the ring 14 to allow formation of laser weldment 16.

It is obvious to those skilled in the art of metallurgical bonding and brazing that the order of assembly is not invariant and may be dictated by good engineering practice.

Figure 4:
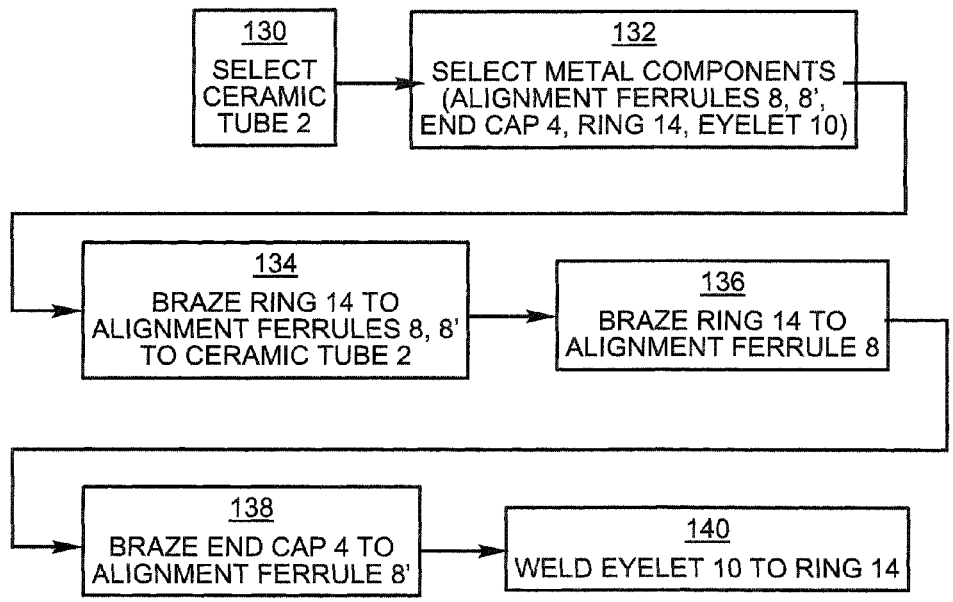
FIG. 4 presents a flow diagram for a method of component assembly.

However, it has been learned through experimentation that the steps represented schematically in FIG. 4 as steps 134, 136, and 138 must be performed in a single braze operation simultaneously. At the second end, the end cap 4 may be bonded to the alignment ferrule 8' at the same time that the alignment ferrule 8' is bonded to the ceramic tube 2. Similarly, at the first end, the ring 14 may be bonded to the alignment ferrule 8 in a single operation, when the alignment ferrule 8 is bonded to the ceramic tube 2. The ring 14 is also bonded to the alignment ferrule 8 and the end cap 4 is bonded to the alignment ferrule 8' before an electronics package is placed inside the assembly 12. Then the preferred last step is to laser weld the eyelet 10 to the ring 14. In this manner high temperature brazing operations are conducted without the electronics being present and thereby avoiding submission of the electronics to a high and damaging temperature. The laser welding operation preferably bonds a platinum eyelet 10 to a platinum ring 14, thus avoiding temperature induced damage to any packaged electronics.

A method of forming the component assembly 12 is presented in FIG. 4. In step 130 a ceramic tube 2 is selected and is preferably partially stabilized tetragonal zirconia polycrystal. This material is strong and bonds by brazing to titanium and titanium alloys.

In step 132 metal components are selected, specifically the alignment ferrules 8, 8', end cap 4, eyelet 4, and ring 14 are selected from biocompatible materials that can be bonded together to from a hermetic component assembly 12. In a preferred embodiment, as discussed previously, the alignment ferrules 8, 8' are comprised of titanium or a titanium alloy. They also have a lip 24 and ferrule face 28 to facilitate self-alignment.

The end cap 4 is comprised of a noble metal, preferably platinum. It is sized to fit snugly to the ferrule face 26 and to contact the lip 24 of the alignment ferrule 8'.

The ring 14 is selected to fit snugly in the alignment ferrule 8 and to contact the ferrule face 26 and to contact the lip 24. It is comprised of a noble metal, preferably platinum.

The eyelet 10 is selected to contact the ring 14. The eyelet 10 is comprised of a noble metal, preferably platinum. It is selected to self-align with the ring 14 by alignment tab 30 fitting snugly inside the hollow ring 14.

In step 134 the alignment ferrules 8, 8' are brazed to the ceramic tube 2 of step 130.

In step 136 the ring 14 is brazed to the alignment ferrule 8. A hermetic bond results with braze joint 21 forming. The platinum ring is readily brazed to the titanium alignment ferrule.

In step 138 the end cap 4 is metallurgically bonded, preferably by brazing, to alignment ferrule 8'. Lastly, eyelet 10 is metallurgically bonded, preferably by welding and most preferably by laser welding, to ring 14. The resulting component assembly 12 is thus hermetically sealed and ready for implantation in living tissue.

Steps 134, 136, and 138 are performed in a single braze operation simultaneously. This step is performed at about $10^{-4}$ Torr or higher vacuum. This simultaneous processing avoids detrimental formation of intermetallics that would occur upon reheating leading to a loss of strength and hermeticity in the joints. After braze bonding the assembly is vacuum cooled to room temperature in the furnace to avoid oxidation of the titanium, which could lead to discoloration and joint brittleness.

Thus, in accordance with this invention, it is now possible to form an implantable hermetically sealed ceramic tube, suitable for containing electronic components, that can serve as a microstimulator or a microsensor by a low-cost, high yield process that utilizes bonding processes for zirconia, titanium and platinum components which utilize self-alignment features. This is a surprising result since performing the braze bonding operation stepwise rather than simultaneously resulted in inadequate bond joints for implantation.

Obviously, many modifications and variations of the present invention are possible in light of the above teachings. It is therefore to be understood that, within the scope of the appended claims, the invention may be practiced otherwise than as specifically described.

GLOSSARY

Terms are generally to be interpreted within the context of the specification and claims. The following terms of art are defined and are to be interpreted by these definitions. Terms that are not defined here shall be interpreted according to definitions from the ASM Metals Reference Book, $3^{rd}$ Edition, 1993, which is included by reference in its entirety.

Biocompatible. The ability of a long-term implantable medical device to perform its intended function, with the desired degree of incorporation in the host, without eliciting any undesirable local or systemic effects in that host. Regulatory agencies require that implanted objects or devices within the human body be biocompatible.

Bond. In welding, brazing, or soldering, the junction of joined parts. Where filler metal is used, it is the junction of the fused metal and the heat-affected base metal.

Braze. Bonding by heating an assembly to suitable temperature and by using a filler metal having a liquidus above 450° C. (840° F.) and below the solidus of the base metal. The filler metal is distributed between the closely fitted faying surfaces of the joint by capillary action.

Butt joint. A joint between two abutting members lying approximately in the same plane.

Filler metal. Metal added in making a brazed, soldered, or welded joint.

Foil. Metal in sheet form less than 0.15 mm (0.006 inches) thick.

Hermetic. Completely sealed by fusion, soldering, brazing, etc., especially against the escape or entry of air or gas.

Implant. To insert or embed an object or a device surgically.

Interlayer. See Foil.

Joined. Fastened together by brazing, welding, or soldering.

Liquidus. In a phase diagram, the locus of points representing the temperatures at which the various compositions in the system begin to freeze on cooling or finish melting on heating.

Microstimulator. An implantable, biocompatible device having dimensions that are less than about 6 mm diameter and 60 mm in length that is capable of sensing or stimulating electrical signals within living tissue.

Noble metal. A metal with marked resistance to chemical reaction, particularly to oxidation and to solution by inorganic acids.

Roll bonding. The same as roll welding and forge welding. A solid-state process where metals are forced together while hot by applying very high pressure that is asserted by rolls to form plate, sheet or foil material and not complex shapes. No filler material is used to achieve roll bonding.

Soldering. A group of processes that join metals by heating them to a suitable temperature below the solidus of the base metals and applying a filler metal having a liquidus not exceeding 450° C. (840° F.). Molten filler metal is distributed between the closely fitted surfaces of the joint by capillary action.

Solid-state welding. A group of processes that join metals at temperatures essentially below the melting points of the base materials, without the addition of a brazing or soldering filler metal. Pressure may or may not be applied to the joint.

Solidus. In a phase diagram, the locus of points representing the temperatures at which various composition stop freezing upon cooling or begin to melt upon heating.

What is claimed is:

1. A component assembly for use in living tissue comprising:
    a ceramic part;
    at least one titanium or titanium alloy metal alignment ferrule that is braze bonded to said ceramic part;
    a ring comprised of a noble metal that is brazed to said alignment ferrule;
    said metal alignment ferrule further comprising at least one integral lip that enables alignment of said ceramic part and said ring; and
    an eyelet comprised of a noble metal that is metallurgically bonded to said ring.

2. The component assembly of claim 1 further comprising an end cap comprised of a noble metal that is metallurgically bonded to said at least one titanium or titanium alloy metal alignment ferrule.

3. The component assembly of claim 1 wherein said noble metal is selected from the group consisting of platinum, iridium, and their alloys.

4. The component assembly of claim 1 wherein said at least one titanium or titanium alloy metal alignment ferrule has concentric lips that define a double cup.

5. The component assembly of claim 1 wherein said ceramic part is comprised of partially stabilized tetragonal zirconia polycrystal material.

6. A component assembly comprising:
    an implantable miniature device having a ceramic tube adapted to contain electronic components and an alignment ferrule comprised of titanium or its alloys brazed thereto and having means for centering said ceramic tube therein;
    a noble metal ring brazed to said alignment ferrule; and
    a noble metal eyelet having alignment means for centering said ring therein.

7. The component assembly of claim 6 wherein said ceramic tube is comprised of partially stabilized tetragonal zirconia polycrystal material.

8. The component assembly of claim 6 wherein said noble metal is selected from the group consisting of platinum, iridium, and their alloys.

9. The component assembly of claim 6 wherein said ring is laser welded to said eyelet.

10. The component assembly of claim 6 wherein said eyelet comprises means for centering said ring, which consists of an alignment tab with an alignment face that contacts said ring.

11. The component assembly of claim 6 wherein said component assembly further comprises an end cap that is comprised of a noble metal, said end cap is brazed to said alignment ferrule.

12. The component assembly of claim 6 wherein said alignment ferrule is coated with iridium.

* * * * *